(12) United States Patent
Mahmoud et al.

(10) Patent No.: US 10,933,403 B1
(45) Date of Patent: Mar. 2, 2021

(54) METHODS FOR THE DECORATION OF CARBON NANOPARTICLES WITH HAFNIUM PROMETHIUM OXIDE NANOWIRES FOR ENERGY APPLICATIONS

(71) Applicant: King Abdulaziz University, Jeddah (SA)

(72) Inventors: Waleed Elsayed Mahmoud, Jeddah (SA); Ahmed Abdullah Salem Al-Ghamdi, Jeddah (SA); Yusuf Abdulaziz Al-Turki, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/004,236

(22) Filed: Aug. 27, 2020

(51) Int. Cl.
| | | |
|---|---|---|
| *B01J 23/10* | (2006.01) | |
| *B01J 21/18* | (2006.01) | |
| *B01J 35/00* | (2006.01) | |
| *C07C 29/153* | (2006.01) | |
| *B01J 37/02* | (2006.01) | |

(52) U.S. Cl.
CPC ............... *B01J 23/10* (2013.01); *B01J 21/18* (2013.01); *B01J 35/004* (2013.01); *B01J 35/0013* (2013.01); *B01J 37/0221* (2013.01); *B01J 37/0228* (2013.01); *C07C 29/153* (2013.01)

(58) Field of Classification Search
CPC ........ B01J 23/10; B01J 21/18; B01J 35/0013; B01J 35/004; B01J 37/0221; B01J 37/0228; C07C 29/153
See application file for complete search history.

(56) References Cited

U.S. PATENT DOCUMENTS

| | | | |
|---|---|---|---|
| 8,182,786 B2 | 5/2012 | O'Brien et al. | |
| 9,999,870 B2 | 6/2018 | O'Brien | |
| 2008/0107586 A1 | 5/2008 | Smalley et al. | |
| 2019/0386105 A1 | 12/2019 | Grimes et al. | |

FOREIGN PATENT DOCUMENTS

JP        5774180 B1    7/2015

*Primary Examiner* — James A Fiorito
(74) *Attorney, Agent, or Firm* — W & C IP

(57) ABSTRACT

Carbon nanoparticles are decorated with ultrafine hafnium promethium nanowires. Exemplary nanowires of hafnium promethium oxide (e.g., $Hf_{0.7}Pm_{0.3}O_2$) have been fabricated. The carbon nanoparticles decorated with hafnium promethium nanowires may be used in reactions for reducing carbon dioxide to methanol, and have applications as a photocatalyst for energy applications.

18 Claims, 4 Drawing Sheets

METHODS FOR THE DECORATION OF CARBON NANOPARTICLES WITH HAFNIUM PROMETHIUM OXIDE NANOWIRES FOR ENERGY APPLICATIONS

FIELD OF THE INVENTION

The invention is generally related to photocatalysts and particularly methods to decorate carbon nanoparticles with ultrafine nanowires of hafnium promethium oxides. The photocatalysts have particular utility in the production of methanol from carbon dioxide.

BACKGROUND

The conversion of solar energy into chemical energy has presented many challenges. It would be advantageous to use solar energy to prompt photocatalytic reduction of gases into renewable organic and fossil fuels, such as carbon monoxide, methane, formic acid, nitrobenzene and ethanol. Various photocatalysts were developed for gas reduction, and examples include $AgS_2$, $AgInSe_2$, $GaSe$, $CdSe$, $NiO$, $Co_2O_3$, $Co(OH)_2$, $SiO_2$, $TiO_2$, $CeO_2$, $MgAlO_3$ and $ZnO$. These nanostructures are capable of absorbing ultraviolet light to generate electron-hole pairs. Unfortunately, the photo-generated electron-hole pairs suffer from fast recombination, which hinder their effectiveness as photo-catalysts.

Alternative approaches have been employed to improve the photo-generated charge separation. These have included the doping with noble metals, surface photo-sensitization, and the preparation of quantized ZnO nanocrystallites. Although these approaches have produced improvements of photogenerated electron/hole pairs recombination, the ability of these modifications to convert the gases into renewable organic and fossil fuels with high yield was very low, which hinder their practical use in real life. Recently, carbon-based materials such as carbon black, graphite, carbon nanotubes and graphene have been of intense interest owing to their high conductivity and chemical stability.

Their remains a need for alternative photocatalysts, particularly for us in the production of methanol from carbon dioxide.

SUMMARY

An object of the invention is to provide a carbon nano-architecture, photocatalyst which comprises carbon nanoparticles decorated with ultrafine nanowires of hafnium promethium oxides.

It is another object of the invention to provide a carbon nanoarchitecture, photocatalyst having carbon nanoparticles decorated with ultrafine nanowires of the formula $Hf_xPm_yO_z$, wherein, x ranges from 0.1 to 2, y ranges from 0.1 to 1, and z ranges from 1 to 4. The nanowires typically have a diameter ranging from 4 nm to 6 nm, and a height from the surface of the carbon nanoparticle ranging from 50 nm to 70 nm. In particular embodiments, the nanowires of formula $Hf_{0.7}Pm_{0.3}O_2$ have an average length of 60 nm and a diameter of the 5 nm.

In a preferred embodiment, each of said one or more nanoparticles are decorated with the nanoparticle ultrafine nanowires of formula $Hf_{0.7}Pm_{0.3}O_2$. The carbon nanoparticles have a diameter of 50 to 300 nm such as 50 nm, 100 nm, 150 nm, 200 nm, 250 nm or 300 nm, and, preferably, the carbon nanoparticles have a diameter ranging from 150 nm to 200 nm. The preferred ratio of carbon nanoparticles to ultrafine nanowires is 1:0.75 by weight.

The carbon nanoparticles decorated with ultrafine hafnium promethium oxide (e.g., $Hf_{0.7}Pm_{0.3}O_2$) nanowires can reduce the $CO_2$ to $CH_3OH$ under UV illumination. Good results have been obtained at a wavelength of 7=254 nm and UV power of 10 mW/cm². Methanol can be prepared from carbon dioxide in the presence of the photocatalyst of this invention in the amount of 573.6 $\mu mol/g_{cat}$ after 2 h of UV irradiation.

BRIEF DESCRIPTION OF THE DRAWINGS

The patent or application file contains at least one drawing executed in color. Copies of this patent or patent application publication with color drawings will be provided by the Office upon request and payment of the necessary fee.

The accompanying drawings, which are incorporated in and constitute a part of this specification, illustrate embodiments of the invention and, together with a general description of the invention given above, and the detailed description given below, serve to explain the invention.

FIG. 1A shows the nanoparticles before decoration. FIG. 1B shows the decorated carbon nanoparticles with ultrafine $Hf_{0.7}Pm_{0.3}O_2$ nanowires. FIG. 1C is a high resolution SEM image for one $Hf_{0.7}Pm_{0.3}O_2$ nanowire C.

DETAILED DESCRIPTION

Figure 1A:
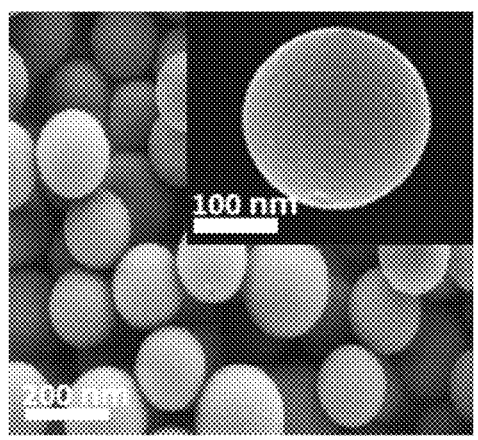
FIG. 1A-C are scanning electron micrograph (SEM) images for the carbon nanoparticles.

The present disclosure provides a carbon nanoarchitecture, photocatalyst, methods of making the photocatalyst, and applications thereof.

By nanoarchitecture, also referred to herein as photocatalyst we mean one or more carbon nanoparticles, wherein each of the one or more carbon nanoparticles comprises a surface (i.e., the outer surface) decorated with ultrafine nanowires of hafnium promethium oxides. The hafnium promethium oxides have the general formula $Hf_xPm_yO_z$, wherein.

x ranges from 0.1 to 2, such as 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0, y ranges from 0.1 to 1, such as 0.1, 0.2, 0.3, 0.4, 0.5, 0.6, 0.7, 0.8, 0.9, 1.0, and z ranges from 1 to 4 and most preferably from 1.8 to 2.3 (e.g., 1.8, 1.9, 2.0, 2.1, 2.2, and 2.3).

In some embodiments, this invention provides a method of forming the photocatalyst by a hydro-thermal approach. In particular, the following steps would be performed.
1) Purifying carbon nanoparticles.
2) Treating the purified carbon nanoparticles with hafnium salt to form carbon nanoparticles coated with hafnium seeds.
3) Treating the carbon nanoparticles coated with hafnium seeds with a hafnium salt and a promethium salt to form one or more carbon nanoparticles comprising a surface decorated with ultrafine nanowires of formula $Hf_xPm_yO_z$, wherein, x ranges from 0.1 to 2, y ranges from 0.1 to 1, and z ranges from 1 to 4 (preferably 1.8 to 2.3).

In a preferred embodiment, the carbon nanoparticles have a diameter of 50 to 300 nm such as 50 nm, 100 nm, 150 nm, 200 nm, 250 nm or 300 nm.

In a preferred embodiment, the carbon nanoparticles have a diameter in the range of 150 nm to 200 nm.

In some embodiments, the hafnium source is a hafnium salt selected from a group consisting of but not limited to hafnium chloride, hafnium nitrate, hafnium oxalate, hafnium sulfate, and hafnium acetate. In a preferred embodiment, hafnium nitrate is the best source of hafnium for growing nanowires on the surface of said the one or more carbon nanoparticles.

Preferably, the source of the oxide is preferably sodium hydroxide, but can also be potassium hydroxide, ammonium hydroxide, or calcium hydroxide.

In a preferred embodiment, the promethium source is a promethium salt selected from a group consisting of but not limited to promethium chloride, promethium nitrate, promethium oxalate, and promethium acetate. Preferably, promethium nitrate is the source. The optimum stoichiometry of the promethium with respect to the hafnium ranges from 0.27 to 0.33 (e.g., 0.3).

In a preferred embodiment, the nanoarchitecture comprises one or more carbon nanoparticles. Each of the one or more carbon nanoparticles have a surface decorated with ultrafine nanowires of hafnium promethium oxides (e.g., $Hf_{0.7}Pm_{0.3}O_2$). The preferred ratio of carbon nanoparticles to ultrafine nanowires of hafnium promethium oxides (e.g., $Hf_{0.7}Pm_{0.3}O_2$) is 1:0.75 by weight. The nanowires of formula $Hf_{0.7}Pm_{0.3}O_2$ have an average length ranging from 50 nm to 70 nm (e.g., 60 nm) and an average diameter ranging from 4 nm to 6 nm (e.g., 5 nm).

The photocatalyst is synthesized using in a hydrothermal approach comprising refluxing carbon nanoparticles in acidic conditions such as in nitric acid followed by washing in a mixture of water and ethanol to afford purified carbon nanoparticles. A suspension is formed with the purified carbon nanoparticles in alcohol, such as but not limited to methanol, ethanol or isopropanol, and with hafnium acetate. This is followed by a reaction with a mixture of hafnium nitrate and promethium nitrate in the presence of hexamine. Hexamine has been found to be responsible for the growth of $Hf_{0.7}Pm_{0.3}O_2$ on the surface on the carbon in the form of nanowires, and experiments with other reagents have not been shown to bet able to do that job. This processing has yielded decorated carbon nanoparticles with $Hf_{0.7}Pm_{0.3}O_2$ nanowires.

The photocatalyst exhibits an absorption energy band at 2.8 eV.

Figure 1B:
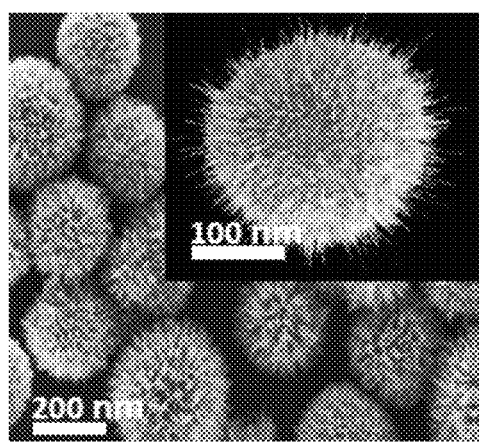
Figure 1C:
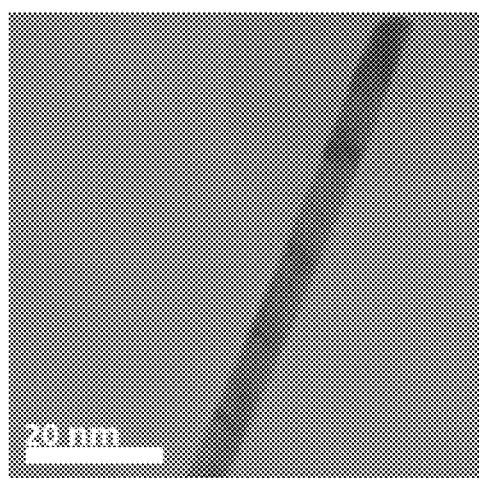
Figure 2:
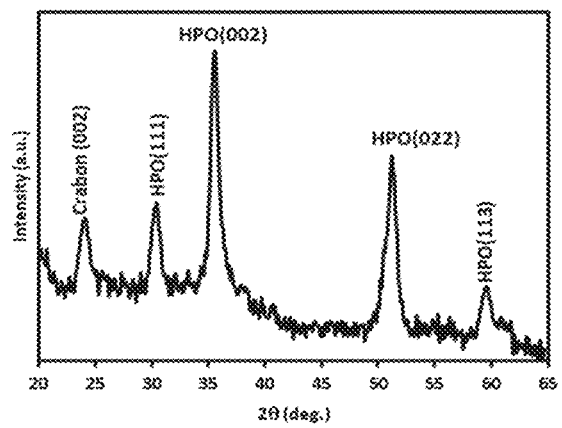
FIG. 2 is a graph with x-ray diffraction (XRD) patterns of the decorated carbon nanoparticles with ultrafine $Hf_{0.7}Pm_{0.3}O_2$ nanowires.

Preferably, the carbon nanoparticles used to synthesize the photocatalyst generally have a spherical shape, and the nanoparticles have an average diameter of 150-200 nm as indicated by the SEM image in FIG. 1A. The average length of the grown hafnium promethium oxide (e.g., $Hf_{0.7}Pm_{0.3}O_2$) nanowires is around 60 nm (FIG. 1B) and the diameter of these nanowires is around 5 nm as shown in FIG. 1C. With reference to FIG. 2, the XRD showed a broad peak at $2\theta=24.5°$, which is the characteristic peak of the graphite plane (002) with $d_{002}$ spacing of 0.33 nm corresponding to carbon nanoparticles. The XRD also showed peaks corresponding to (111). (002), (022) and (113) reflection of the $HfO_2$ cubic crystal structure (JCPDS-Card no. 73-1273). There are no other peaks for Hf bi-products or promethium or oxide compounds in the XRD patterns, which indicates dissolving of the promethium atoms into the hafnium oxide crystal structure.

In some embodiments, the present invention provides carbon nanoparticles decorated with ultrafine hafnium promethium oxide (e.g., $Hf_{0.7}Pm_{0.3}O_2$) nanowires that efficiently suppress the recombination of the photogenerated electron-hole pairs.

The photocatalyst according to the present invention can be used for energy applications.

The photocatalyst according to the present invention can be used for reduction reactions.

The photocatalyst according to the present invention can be used to reduce carbon dioxide to produce methanol.

In another embodiment, the present invention provides carbon nanoparticles decorated with ultrafine hafnium promethium oxide (e.g., $Hf_{0.7}Pm_{0.3}O_2$) nanowires that can reduce the $CO_2$ to $CH_3OH$ under UV illumination of wavelength of =254 nm and UV power of 10 mW/cm$^2$. The wavelength ($\lambda$) can range from 200-350 nm (e.g., 245 nm, 254 nm, etc.). The carbon nanoparticles decorated with ultrafine $Hf_{0.7}Pm_{0.3}O_2$ nanowires are able to produce methanol from carbon dioxide with amount of 573.6 µmol/$g_{cat}$ after 2 h.

In some embodiment, the photocatalyst comprising decorated surface of a carbon nanoparticle with ultrafine nanowires of formula $Hf_{0.7}Pm_{0.3}O_2$ exhibits high photostability.

In another embodiment, the present invention provides carbon nanoparticles decorated with ultrafine hafnium promethium oxide (e.g., $Hf_{0.7}Pm_{0.3}O_2$) nanowires that can be used 1000 to 7000 times such as, 1000, 2000, 3000, 4000, 5000, 6000 or 7000 while preserving their photocatalysis performance.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a". "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1. Decoration of Carbon Nanoparticles with Ultrafine $Hf_{0.7}Pm_{0.3}O_2$ Nanowires The carbon nanoparticles (average diameter between 150-200 nm) were supplied by Bayer Company with ASTM code N221. The supplied carbon nanoparticles were purified prior to use by refluxing 2 g in 200 ml of nitric acid (1M) at 120° C. for 3 h. The treated carbon nanoparticles were washed by a mixture of water and ethanol then followed by drying in vacuum oven at 70° C. for 10 h. The purified carbon nanoparticles were dispersed in 50 ml of ethanol and sonicated for 30 min. Then, 1.2 mM of hafnium acetate was added to the suspended carbon nanoparticles in ethanol followed by the drop-wise addition of 5 ml of sodium hydroxide (2 mM). The solution was stirred for 20 min and then collected by centrifuge at 12000 rpm for 2 min. The powder was dried in a vacuum oven at 60° C. for 45 min. The resulting carbon/hafnium powder was dispersed in 30 ml of deionized water and stirred for 30 min. Then, 0.7 mM of hafnium nitrate, 0.3 mM of promethium nitrate and 10 mg of hexamine was added simultaneously to the dispersed carbon/hafnium powder in the deionized water and stirred for 45 min at 80° C. The final powder was collected by filter paper and washed several times with acetone/isopropanol mixture to remove the excess of hexamine. FIG. 1A shows SEM image of the as-received carbon nanoparticles which have a spherical shape like nanoparticles with average diameter of 150-200 nm. FIG. 1B shows SEM image of the grown $Hf_{0.7}Pm_{0.3}O_2$ nanowires on the surface of the carbon nanoparticles. The average length of the $Hf_{0.7}Pm_{0.3}O_2$ nanowires is around 60 nm. The diameter of these nanowires is around 5 nm as shown in FIG. 1C. FIG. 2 shows the XRD of the decorated carbon nanoparticles with $Hf_{0.7}Pm_{0.3}O_2$ nanowires. The XRD showed a broad peak at $2\theta=24.5°$, which is the characteristic peak of the graphite plane (002) with $d_{002}$ spacing of 0.33 nm corresponding to carbon nanoparticles. The XRD showed also peaks corresponding to (111), (002), (022) and (113) reflection of the $HfO_2$ cubic crystal structure (JCPDS-Card no. 73-1273). There are no other peaks for Hf bi-products or promethium or oxide compounds in the XRD patterns, which indicate the dissolving of the promethium atoms into the hafnium oxide crystal structure.

Example 2. The Optical Absorption of the Decorated Carbon Nanoparticles with Ultrafine $Hf_{0.7}Pm_{0.3}O_2$ Nanowires About 10 mg of the decorated carbon nanoparticles with ultrafine $Hf_{0.7}Pm_{0.2}$ nanowires were dispersed in 5 ml of isopropanol and sonicated in ultrasonic bath for 25 min till a homogenous solution formed. The suspension solution of the decorated carbon nanoparticles with ultrafine $Hf_{0.7}Pm_{0.3}O_2$ nanowires was inserting in quartz cuvette with width of 1 cm. The optical absorption spectroscopy was measured using JASCO-780-UV-Vis spectrophotometer.

Figure 3A:
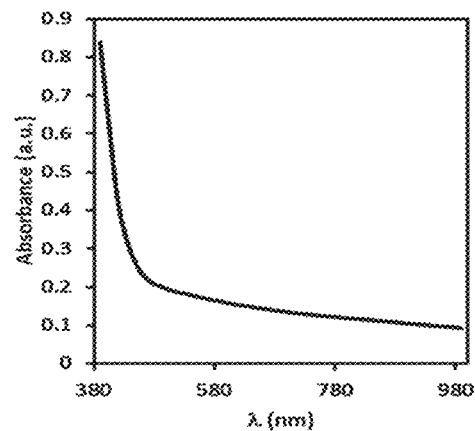
FIGS. 3A and 3B are, respectively, the absorption spectra of the decorated carbon nanoparticles with ultrafine $Hf_{0.7}Pm_{0.3}O_2$ nanowires (FIG. 3A), and Tauc's plot of the decorated carbon nanoparticles with ultrafine $Hf_{0.7}Pm_{0.3}O_2$ nanowires (FIG. 3B).
Figure 3B:
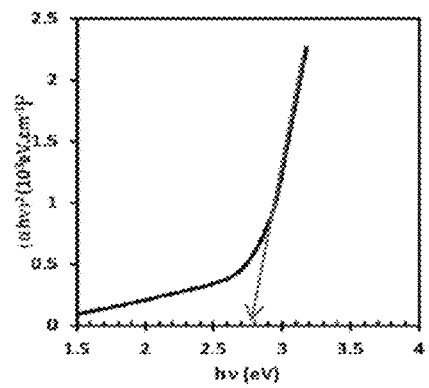

FIG. 3A shows the optical absorption of the decorated carbon nanoparticles with ultrafine $Hf_{0.7}Pm_{0.3}O_2$ nanowires. FIG. 3B shows the Tauc's relation, which indicates that the optical band gap of the decorated carbon nanoparticles with ultrafine $Hf_{0.7}Pm_{0.3}O_2$ nanowires is around 2.8 eV.

Figure 4:
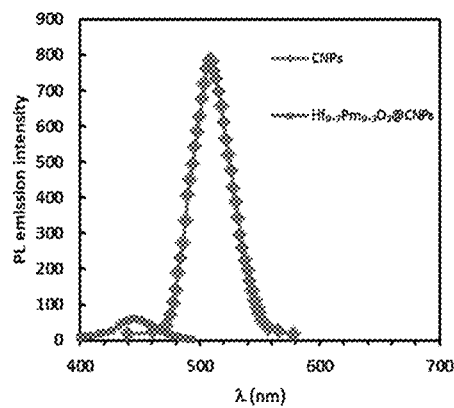
FIG. 4 is a graph of the luminescence spectra of the carbon nanoparticles before and after their decoration with ultrafine $Hf_{0.7}Pm_{0.3}O_2$ nanowires.

Example 3. The Luminescence Spectra of the Decorated Carbon Nanoparticles with Ultrafine $Hf_{0.7}Pm_{0.3}O_2$ Nanowires About 10 mg of the decorated carbon nanoparticles with ultrafine $Hf_{0.7}Pm_{0.3}O_2$ nanowires were dispersed in 5 ml of isopropanol and sonicated in ultrasonic bath for 25 min till a homogenous solution formed. The suspension solution of the decorated carbon nanoparticles with ultrafine $Hf_{0.7}Pm_{0.3}O_2$ nanowires was inserting in quartz cuvette with width of 1 cm. The luminescence spectra were measured using PerkinElmer-LS55 spectrophotometer. FIG. 4 shows the luminescence spectra of the carbon nanoparticles before and after the decoration of their surfaces with ultrafine $Hf_{0.7}Pm_{0.3}O_2$ nanowires. The decoration of the surface of carbon nanoparticles reduced the luminescence intensity. This means the growth of ultrafine $Hf_{0.7}Pm_{0.3}O_2$ nanowires along the surface of the carbon nanoparticles suppress the recombination rate of the photogenerated electron-hole pairs, which is important factor for high performance photocatalysis.

Figure 5A:
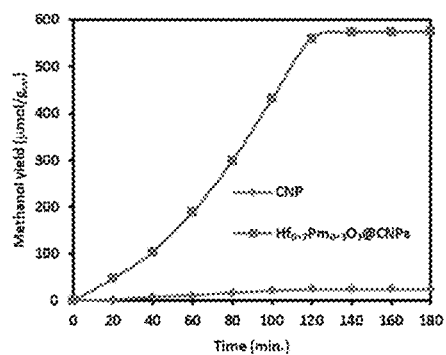
FIGS. 5A and 5B are, respectively, a line graph showing the temporal evolution of the amount of methanol produced in the presence of the carbon nanoparticles before and after the decoration with ultrafine $Hf_{0.7}Pm_{0.3}O_2$ nanowires (FIG. 5A), and a histogram for the amount of methanol produced under UV irradiation for 2 h (FIG. 5B).
Figure 5B:
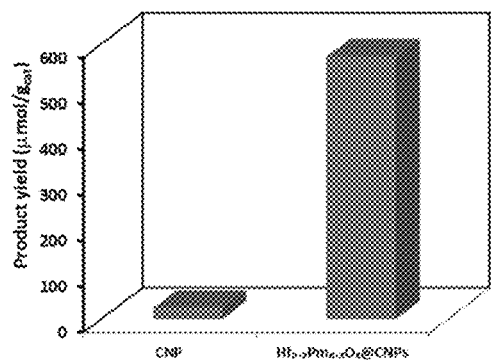

Example 4. The Photocatalytic Reduction of $CO_2$ Using the Decorated Carbon Nanoparticles with Ultrafine $Hf_{0.7}Pm_{0.3}O_2$ Nanowires The photocatalytic reduction process of $CO_2$ is carried out in a photoreactor made of Pyrex with volume capacity of 500 mL. About 1 g of the decorated carbon nanoparticles with ultrafine $Hf_{0.7}Pm_{0.3}O_2$ nanowires was uniformly distributed on a flat surface of Teflon mounted at the center of a photoreactor. A UV lamp with power of 10 mW/cm² and $\lambda=254$ nm is positioned at the center of the photoreactor. The photoreactor is purged with $CO_2$ with flow rate of 10 SCCM for 40 min and then followed by the flow of the water vapor into the photoreactor for 15 min. The experiment is started by switching on the UV lamp. The output gas was identified and quantified by Shimadzu-GC14-C-gas chromatography and Shimadzu-SCL10-ASP-ion chromatography. FIG. 5A shows the time evolution of the amount of produced methanol for the un-decorated carbon nanoparticles and the decorated carbon nanoparticles with ultrafine $Hf_{0.7}Pm_{0.3}O_2$ nanowires. It is noteworthy that the decorated carbon nanoparticles with ultrafine $Hf_{0.7}Pm_{0.3}O_2$ nanowires exhibited the highest photocatalytic reduction of $CO_2$ to $CH_3OH$. The amount of methanol produced during 2 h was found about 573.6 $\mu mol/g_{cat}$. This yield is 10 times greater than the amount produced by using un-decorated carbon nanoparticles as shown in FIG. 5B.

Figure 6:
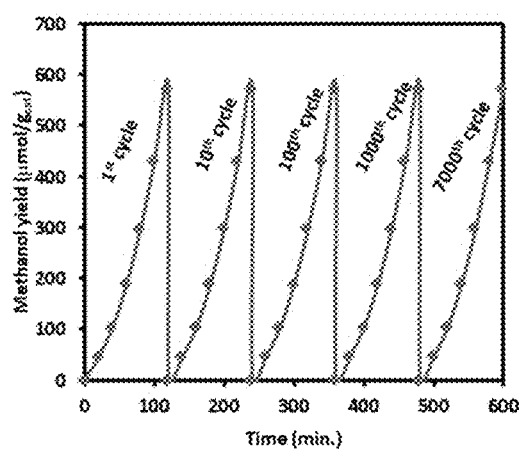
FIG. 6 is a graph showing the photostability and reproducibility of the decorated carbon nanoparticles with ultrafine $Hf_{0.7}Pm_{0.3}O_2$ nanowires at various processing cycles.

Example 5. The Photostability and Reproducibility of the Decorated Carbon Nanoparticles with Ultrafine $Hf_{0.7}Pm_{0.3}O_2$ Nanowires The photocatalytic reduction process of $CO_2$ was carried out using the decorated carbon nanoparticles with ultrafine $Hf_{0.7}Pm_{0.3}O_2$ nanowires, under the same conditions explained in Example 3, at various time intervals as shown in FIG. 6. It is noteworthy that, the decorated carbon nanoparticles with ultrafine $Hf_{0.7}Pm_{0.3}O_2$ nanowires showed high photostability and preserve its photocatalysis performance after multiple consecutive recycling process.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention claimed is:

1. A carbon nanoarchitecture, photocatalyst, comprising one or more carbon nanoparticles, each of said one or more carbon nanoparticles comprising a surface decorated with ultrafine nanowires of formula $Hf_xPm_yO_z$,
    wherein,
    x ranges from 0.1 to 2,
    y ranges from 0.1 to 1, and
    z ranges from 1 to 4.

2. The carbon nanoarchitecture photocatalyst of claim 1, wherein the nanowires are of the formula $Hf_{0.7}Pm_{0.3}O_2$.

3. The carbon nanoarchitecture photocatalyst of claim 1, wherein a ratio of the one or more carbon nanoparticles to the nanowires is 1:0.75 by weight.

4. The carbon nanoarchitecture photocatalyst of claim 1, wherein the carbon nanoarchitecture photocatalyst exhibits an optical band gap of 2.8 eV.

5. The carbon nanoarchitecture photocatalyst of claim 1 wherein the one or more carbon nanoparticles have a mean diameter in the range of 50 to 300 nm.

6. The carbon nanoarchitecture photocatalyst of claim 1 wherein z ranges from 1.8 to 2.3.

7. A method of reducing gases into renewable organic or fossil fuel, comprising exposing the gases to a carbon nanoarchitecture photocatalyst of claim 1 under ultraviolet irradiation for an exposure time sufficient to reduce $CO_2$ to $CH_3OH$.

8. The method of claim 7 wherein the ultraviolet irradiation has a power of 10 $mW/cm^2$ and a λ wavelength of 254 nm.

9. A method of forming a photocatalyst, comprising:
    purifying carbon nanoparticles,
    treating the purified carbon nanoparticles with hafnium salt to form carbon nanoparticles coated with hafnium seeds, and
    treating the carbon nanoparticles coated with hafnium seeds with a hafnium salt and a promethium salt and hexamine to form one or more carbon nanoparticles comprising a surface decorated with ultrafine nanowires of formula $Hf_xPm_yO_z$,
    wherein,
    x ranges from 0.1 to 2,
    y ranges from 0.1 to 1, and
    z ranges from 1 to 4.

10. The method of claim 9 wherein z ranges from 1.8 to 2.3.

11. The method of claim 9 wherein said hafnium salt is selected from the group consisting of hafnium chloride, hafnium nitrate, hafnium oxalate, hafnium sulfate, and hafnium acetate.

12. The method of claim 11 wherein said hafnium salt is hafnium acetate.

13. The method of claim 9 wherein said promethium salt is selected from the group consisting of promethium chloride, promethium nitrate, promethium oxalate, promethium sulfate, and promethium acetate.

14. The method of claim 13 wherein said promethium salt is promethium nitrate.

15. The method of claim 9 wherein a concentration of said promethium salt is in the range of 20 to 50% of the hafnium salt by weight.

16. The method of claim 9 wherein a concentration of said the promethium salt is 30% of the hafnium salt by weight.

17. The method of claim 7, wherein the carbon nanoparticles have a mean diameter in the range of 50 to 300 nm.

18. The method of claim 14, wherein the carbon nanoparticles haves a mean diameter in the range of 150 to 200 nm.

\* \* \* \* \*